United States Patent
Pierson, III et al.

(10) Patent No.: US 6,251,141 B1
(45) Date of Patent: Jun. 26, 2001

(54) BONE CANAL PLUG, METHOD OF MAKING, AND METHOD OF USING

(76) Inventors: Raymond H. Pierson, III, 62 W. Columbia St., Suite C, Orlando, FL (US) 32806; Daniel F. Justin, 185 N. Winding Way, Logan, UT (US) 84321

(*) Notice: Subject to any disclaimer, the term of this patent is extended or adjusted under 35 U.S.C. 154(b) by 0 days.

(21) Appl. No.: 09/178,336

(22) Filed: Oct. 23, 1998

(51) Int. Cl.⁷ ........................................................ A61F 2/30
(52) U.S. Cl. .......................................... 623/23.48; 606/95
(58) Field of Search ............................... 623/23.2, 23.48; 606/95, 92, 93

(56) References Cited

U.S. PATENT DOCUMENTS

| | | |
|---|---|---|
| 4,245,359 | 1/1981 | Stuhmer . |
| 4,276,659 | 7/1981 | Hardinge . |
| 4,302,855 | 12/1981 | Swanson . |
| 4,344,190 | 8/1982 | Lee et al. . |
| 4,447,915 | 5/1984 | Weber . |
| 4,523,587 | 6/1985 | Frey . |
| 4,625,722 | 12/1986 | Murray . |
| 4,686,973 | 8/1987 | Frisch . |
| 4,697,584 | 10/1987 | Haynes . |
| 4,815,454 | 3/1989 | Dozier, Jr. . |
| 5,092,891 | 3/1992 | Kummer et al. . |
| 5,190,551 | 3/1993 | Chin et al. . |
| 5,263,991 | 11/1993 | Wiley et al. . |
| 5,340,362 | 8/1994 | Carbone . |
| 5,383,932 | 1/1995 | Wilson et al. . |
| 5,431,660 | 7/1995 | Burke . |
| 5,531,792 | 7/1996 | Huene . |

FOREIGN PATENT DOCUMENTS

| | | |
|---|---|---|
| 39 37 786 | 7/1990 | (DE) . |
| 0 006 408 | 6/1978 | (EP) . |
| 0 328 848 | 8/1989 | (EP) . |
| 0 379 785 | 8/1990 | (EP) . |
| 0 436 317 | 7/1991 | (EP) . |
| 2 253 564 | 9/1992 | (GB) . |
| 2 324 731 | 11/1998 | (GB) . |
| WO 96/06576 | 3/1996 | (WO) . |
| WO 98/35635 | 8/1998 | (WO) . |

OTHER PUBLICATIONS

The DePuy Cement Restrictor Product Brochure, *Inhibits Distal Migration of Bone Cement*, 1991 DePuy Inc.

*Primary Examiner*—Bruce Snow
(74) *Attorney, Agent, or Firm*—Allen, Dyer, Doppelt, Milbrath & Gilchrist, P.A.

(57) ABSTRACT

A plug system for preventing material from extruding beyond a desired location in a bone tunnel includes a plug member that has an insertion axis extending from a first end and a plurality of interleaving arms disposed about the insertion axis. The arms are affixed at a second end and are flarable at the first end between an insertion position wherein the arms are relatively close packed and a position wherein the arms are flared. A portion of each arm remains in overlapping relation to an adjacent arm. The system further includes an expansion member that has an insertion portion adapted to separate the arms upon progressive entry along the insertion axis from the first end. In use the plug can be inserted either first end first, with the expansion member drawn into the plug by a manipulator, or second end first, with the expansion member driven along the insertion axis.

18 Claims, 7 Drawing Sheets

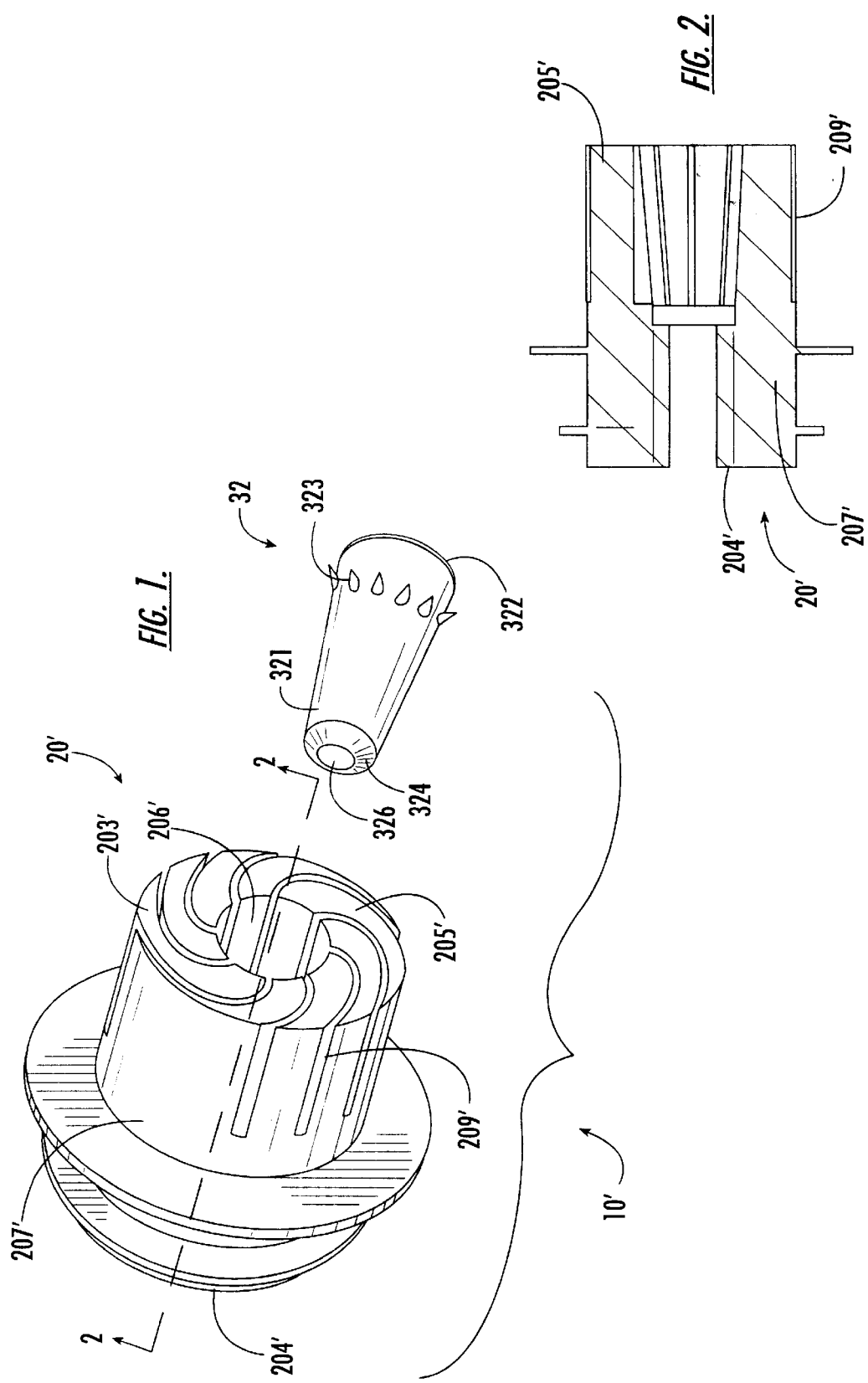

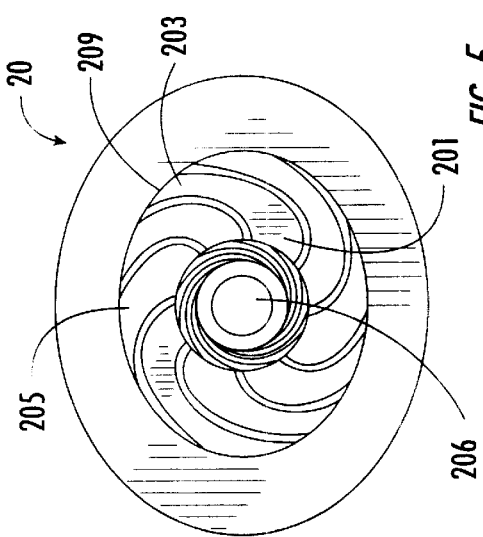
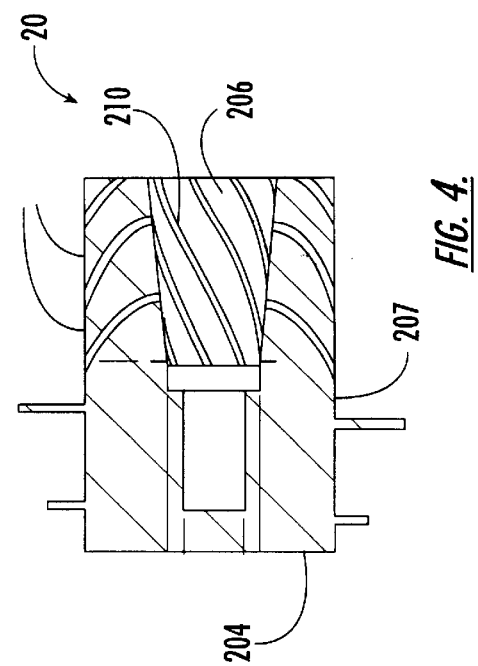
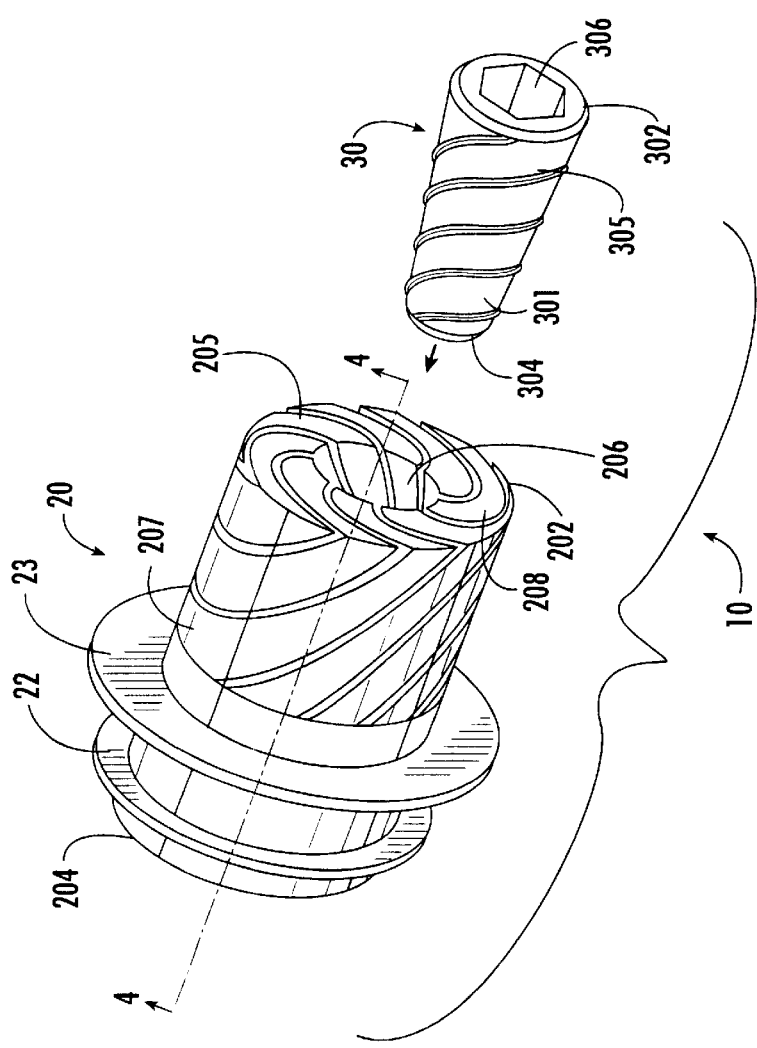

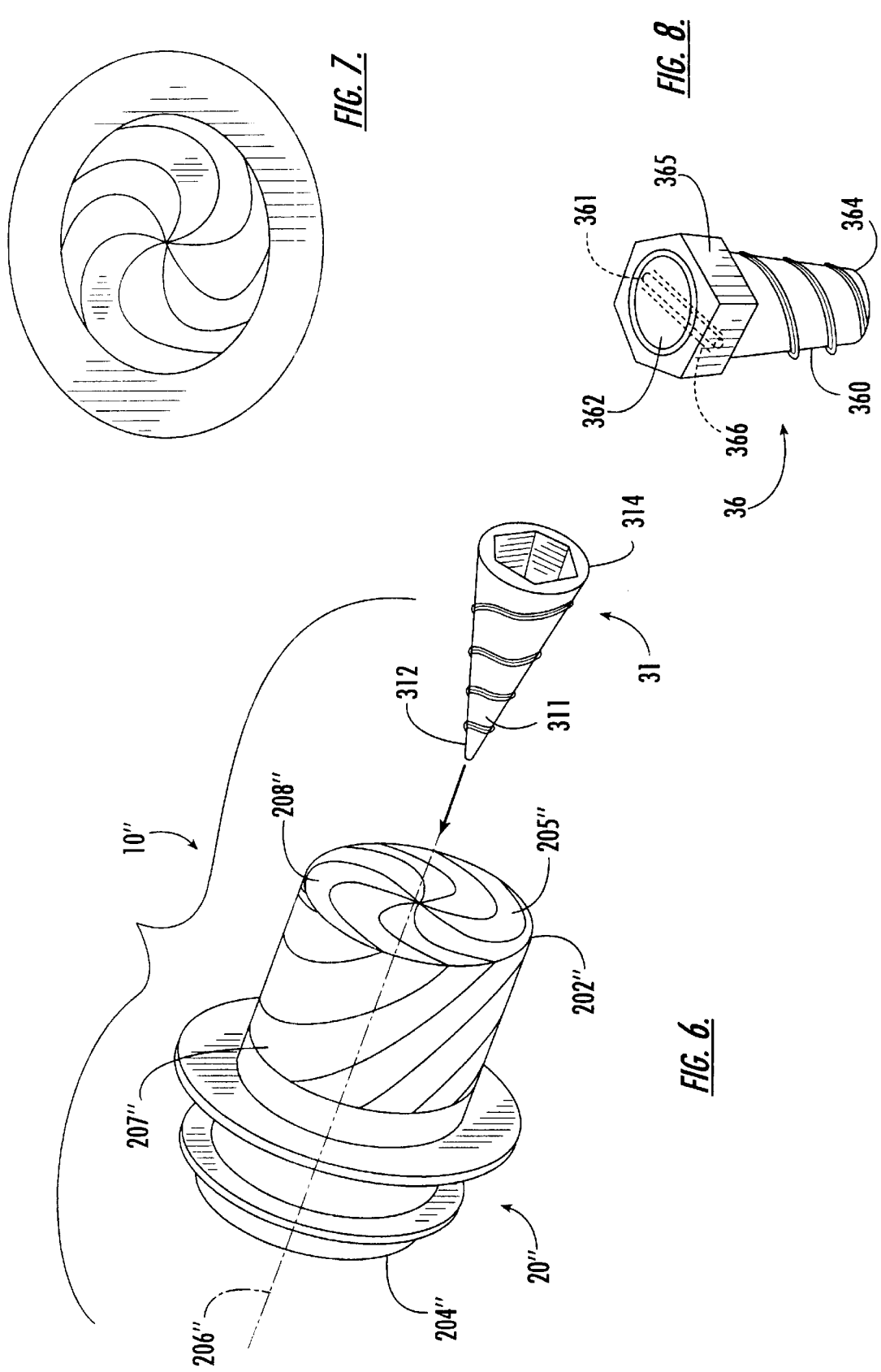

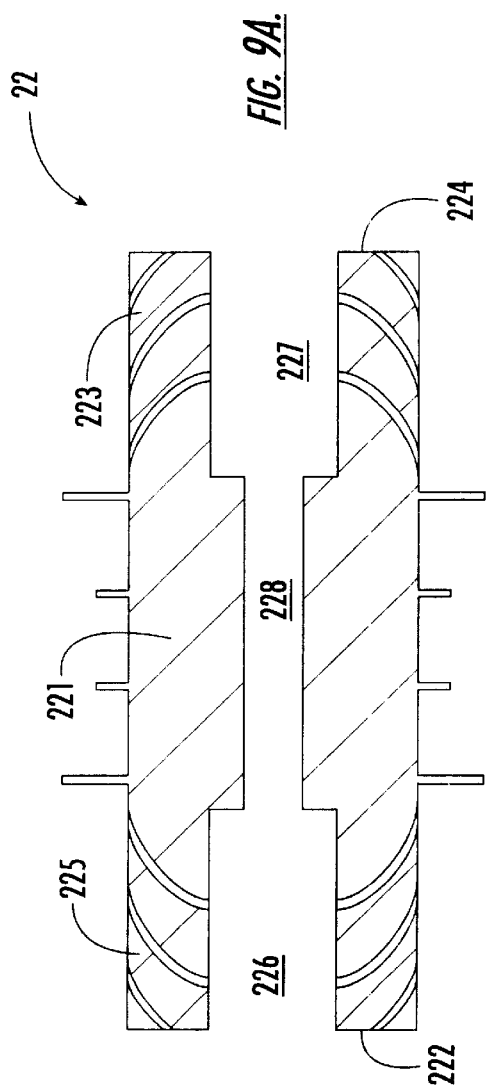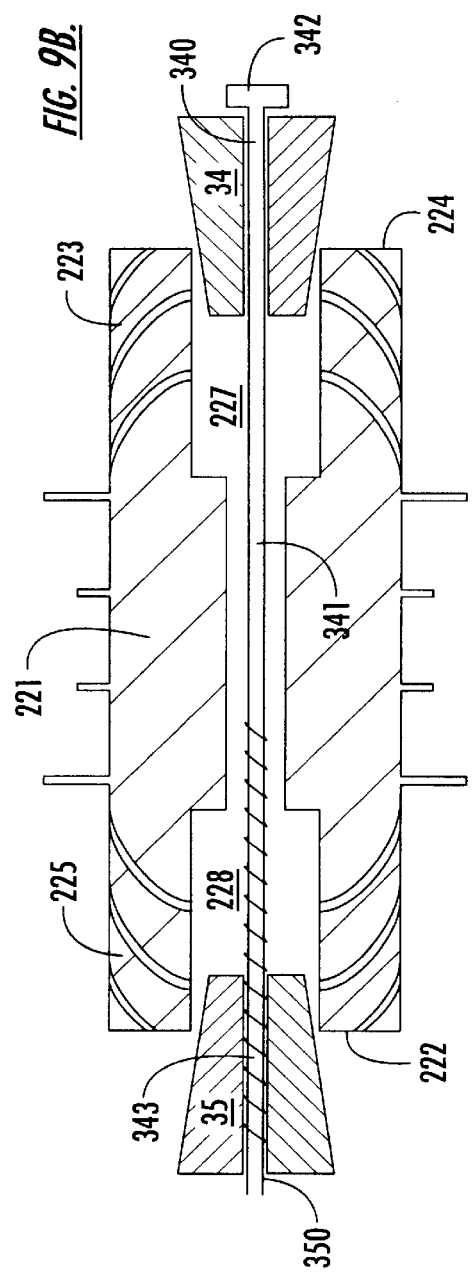

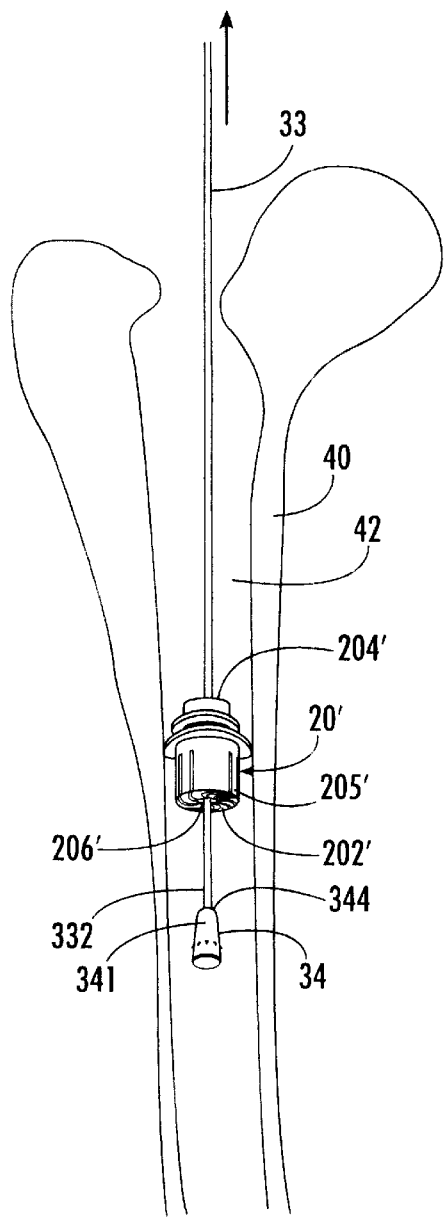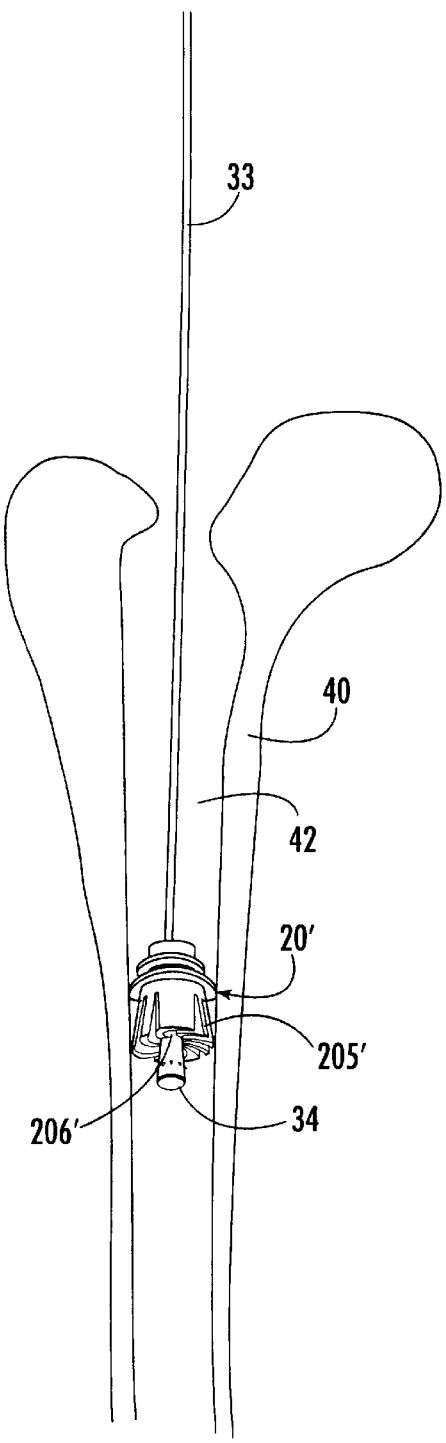
FIG. 10A.
FIG. 10B.

BONE CANAL PLUG, METHOD OF MAKING, AND METHOD OF USING

BACKGROUND OF THE INVENTION

1. Field of the Invention

The present invention relates to articles and methods for blocking a flow of material within a bone canal, and, more particularly, to canal plugs and associated methods.

2. Description of Related Art

In procedures in which an implant is placed within a bone canal it is typical to anchor a distal portion of the implant with a cement material that flows in a liquid state and hardens upon drying. Once sufficient cement has been added under pressure to the canal and permitted to partially dry, the implant distal end is inserted, with a complete drying of the cement achieving a permanent fixation within the canal. In such procedures it is undesirable for the flowing cement to continue beyond the desired implant site, under pressure from the insertion of the implant, since such a displacement would lessen the amount of cement available to achieve optimal fixation.

Such procedures include hip replacement, which involves cutting off the head of the femur, opening the top of the femur, and cleaning out the canal to a length commensurate with the length of the implant stem. The canal is then plugged at the bottom of the cleaned-out space, the implant stem is inserted, and cement is forced around the pin to keep it in place.

The femoral canal plugs used at present are typically provided in a set of incrementally sized high-molecular-weight polyethylene truncated cones that are force-fit into the canal. However, femoral canals are not circular in cross section, but are oval or elliptical. Using a plug having a circular cross section thus leaves gaps surrounding the plugs through which cement may leak and extrude down the canal potentially as far as the knee region.

A further problem can occur with a plug that does not conform sufficiently well to the canal: With modern cement techniques, under the high pressures with which the cement is forced into the canal, plug "blowout" can occur, forcing the plug below the desired location. If these cases go on to require revision surgery at a later time, which occurs with a frequency of 5–10%, a very extensive and potentially destructive (relative to bone stock) operation must be undertaken to remove the cement.

Several intramedullary bone plugs are known in the art, including those that have elements adapted to change shape or expand after insertion into the canal. Among these are those disclosed by Seidel et al. (Eur. Pat. Appl. No. 0 006 408), Haynes (U.S. Pat. No. 4,697,584), Hardinge (U.S. Pat. No. 4,276,659), Swanson (U.S. Pat. No. 4,302,855), Weber (U.S. Pat. No. 4,447,915), Murray (U.S. Pat. No. 4,625,722), Frisch (U.S. Pat. No. 4,686,973), Kummer et al. (U.S. Pat. No. 5,092,891), Wilson (U.S. Pat. No. 5,383,932, and Huene (U.S. Pat. No. 5,531,792).

None of the plugs thus far disclosed, however, adequately conforms to the cross-sectional shape of a bone canal without leaving gaps through which cement may extrude and also is unlikely to experience "blowout."

SUMMARY OF THE INVENTION

It is therefore an object of the present invention to provide a plug for insertion into a bone canal that is adapted to prevent cement passage therepast.

It is an additional object to provide such a plug that resists being displaced distal ward under pressure from cement insertion.

It is a further object to provide a plug that is insertable at a predefined force level.

It is another object to provide a plug having elements that are adapted to closely conform to the wall of a bone canal.

It is yet an additional object to provide a method of making such a bone canal plug.

It is yet a further object to provide a method of inserting such a bone canal plug.

These objects and others are attained by the devices, systems, and methods of the present invention. A first aspect of the invention comprises a plug adapted for insertion into a bone canal. The plug has a plurality of interleaving arms that are disposed about an insertion axis that extends from a first end of the plug. The arms are affixed at a second end and are flarable at the first end. In an insertion position the arms are relatively close packed; in a flared position the arms are radially flared, each arm having a portion remaining in overlapping relation to an adjacent arm.

In a particular embodiment each arm has interleaving arms, each having a generally paisley-like shape in axial cross section, oriented so that the head section faces generally toward the insertion axis and the tail section faces generally radially outward.

Also in a preferred embodiment the plug has an axial cross-sectional shape commensurate with that of its intended site; for example, for use in a femur, a generally oval cross section is preferred. This shape is not intended as a limitation, however, as other shapes will be known by one of skill in the art to be preferable for different intended sites.

The bore is adapted to receive an expansion member for separating the arms upon a progressive insertion thereof along the insertion axis. In a preferred embodiment the expansion member comprises a member tapering outward from a second end, such as a tapered plug, a screw, or a ratchet-type member.

The invention further comprises a method for preventing flowing material from extruding beyond a predetermined location in a bone tunnel. The method comprises the steps of inserting a bone plug such as described above into a bone canal to a desired location. Next the arms are opened to a position wherein the arms are flared. The paisley-like shape permits each arm tail section to remain in overlapping relation to an adjacent arm, thus preventing flowing material from escaping into the tunnel beyond the plug. The arms are continued to be flared until the plug is securely pressed against a wall of the bone tunnel. The plug can be inserted either second or first end first, with the expansion member, respectively, either inserted or pulled into the plug's bore.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side perspective view of an expandable bone plug and an expansion member.

FIG. 2 is a side cross-sectional view of the bone plug of FIG. 1 along 2—2.

FIG. 3 is a side perspective view of an alternate embodiment of an expandable bone plug and an expansion member.

FIG. 4 is a side cross-sectional view along 4—4 of FIG. 3.

FIG. 5 is a top plan view of FIG. 3.

FIG. 6 is a side perspective view of another embodiment of an expandable bone plug.

FIG. 7 is a top plan view of FIG. 6.

FIG. 8 is a side perspective view of an additional embodiment of an expansion member.

FIG. 9A is an axial cross-sectional view of a duplex bone plug.

FIG. 9B is a side perspective view of a duplex bone plug with coupled expansion members.

FIG. 10A illustrates the bone plug of FIG. 3 inserted into a bone canal.

FIG. 10B illustrates the bone plug arms being expanded radially outward with a drawing of an expansion member into the plug bore by a manipulator.

DETAILED DESCRIPTION OF THE PREFERRED EMBODIMENTS

Figure 11A:
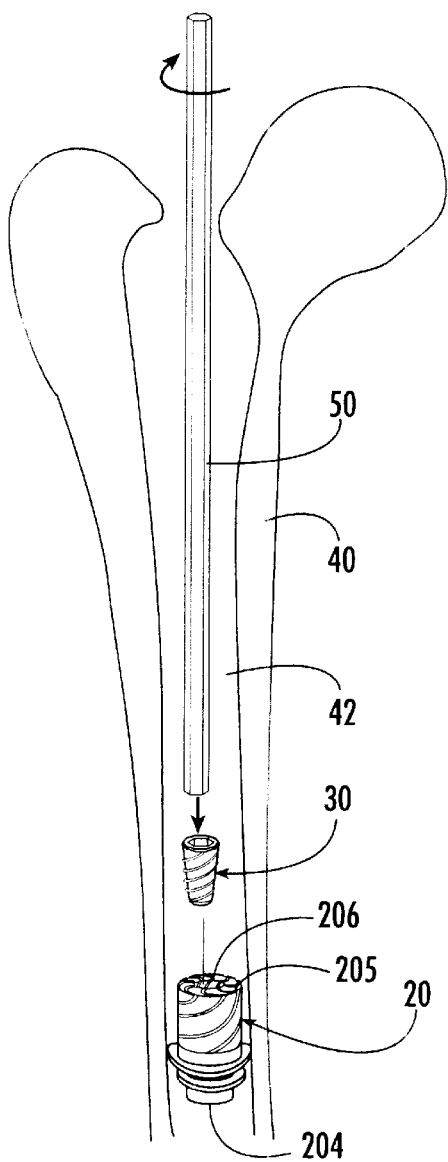
FIG. 11A illustrates the bone plug of FIG. 3 inserted into a lo bone canal.

A description of the preferred embodiments of the present invention will now be presented with reference to FIGS. 1–13.

A first embodiment of a bone plug system 10' of the present invention is illustrated in FIGS. 1 and 2; a second embodiment 10 of the present invention is illustrated in FIGS. 3–5; a third embodiment 10" is illustrated in FIGS. 6 and 7. The systems 10', 10 comprise, respectively, a plug member 20', 20 that has an axial bore 206', 206. In the first embodiment 10' the bore 206' extends through from the first end 202' to a second end 204' that is generally axially opposed to the first end 202'; in the second embodiment, the bore 206 extends from the first end 202 but not completely through to the second end 204. In the third embodiment 10" the plug member 20" has no axial bore; rather an insertion axis 206" extends from the first end 202" to the second end 204".

The plug members 20', 20 have a plurality of interleaving arms 205', 205 disposed about the bore 206', 206. For the plug member 20" the plurality of arms 205" are disposed about the insertion axis 206". The arms 205', 205, 205" are affixed at their second ends 207', 207, 207" adjacent the plug member's second end 204', 204, 204"; the arms 205', 205, 205" are further flarable at their first ends 208', 208, 208" between an insertion position wherein the arms 205', 205, 205" are relatively close packed and a position wherein the arms 205', 205, 205" are flared, each arm 205', 205, 205" remaining in overlapping relation to an adjacent arm (see FIG. 11B).

In a particular embodiment, each arm 205', 205, 205" has a generally paisley-like shape in axial cross section (see FIG. 5), with a paisley head section 201 facing generally toward the bore 206 and a paisley tail section 203 facing generally outward. In addition, each paisley head section 201 is contoured away from the bore 206 in this embodiment to form a generally circular bore 206 in axial cross section when in the close-packed position. In order to ensure that material cannot leak past the plug member 20 during use, the tail sections 203 are sufficiently long that in the flared position each tail section 203 remains in overlapping relation to a portion of an adjacent arm 205.

In the first embodiment of the plug member 20' shown in FIGS. 1 and 2, the tail edge 209' of each arm 205' tail section 203' extends generally along the axial direction. In the second embodiment, shown in FIGS. 3–5, the tail edge 209 of each tail section 203 extends generally helically about the axial direction.

As shown in FIG. 3, the plug member 20 further has a pair of deformable circumferential flanges 22 and 23. The first flange 22 is positioned generally adjacent the second end 204, and the second circumferential flange 23 is positioned in spaced relation to the first flange 22 between the first flange 22 and the first end 202. The second flange 23 preferably has a circumference greater than a circumference of the first flange 22.

Another important feature of the plug member 20', 20, 20" is its axial cross-sectional shape, which is adapted to conform to the shape of the intended placement site. When the plug is for use intrafemorally, for example, the plug member 20 preferably has a generally oval outer shape in axial cross section. For other bone tunnels, it is obvious to one of skill in the art that alternate cross-sectional shapes could be envisaged.

The bone plug systems 10', 10, 10", of the present invention further comprise an expansion member 32, 30, 31 that has an insertion portion 321, 301, 311 adapted to separate the arms 205', 205, 205" upon progressive entry into the bore 206', 206 or along the insertion axis 206". Preferably the expansion member 32, 30, 31 tapers outward from a second end 324, 304, 314 to a first end 322, 302, 312, and has means for being driven at the first end 322, 302, 312. In the first embodiment of FIG. 1, the expansion member 32 comprises a truncated conical element adapted for press fitting within the plug member bore 206'. In this embodiment, the conical element 32 has means for resisting a movement out of the plug member bore 206', such as, but not limited to, barbs 323 facing toward the first end 322. In this embodiment the bore 326 has a narrowed portion adjacent the second end 324, and the driving means may comprise an elongated element that is dimensioned for insertion into the bore 326 but not into the narrowed bore portion.

In the second embodiment of FIG. 3, the expansion member 30 comprises a screw having helical outer threads 305 extending from the second end 304; and the plug member 20 has a helical groove 210 along an inner wall defining the bore 206, the groove 210 adapted for mating with the screw threads 305. The driving means may comprise, but is not intended to be limited to, a hexagonal indentation 306 for mating with a hexagonal driver 50 (see FIG. 11B).

It may be appreciated by one of skill in the art that the plugs and expansion members need not necessarily be separate members; they may, for example, be frangibly joined with a first part of the insertion portion already within the bore or adjacent the insertion axis. Deploying then would comprise pressing upon the expansion member or rotating it until the bonds are broken with the plug, with continued insertion enabled.

In another embodiment, expansion member 30 may be inserted with a device adapted to permit insertion until a predetermined torque level is reached, upon which no further insertion is permitted. Such devices are known in the art, and may include a torque wrench. Having a predetermined torque level permits the surgeon to tailor the insertion force to the state of the patient's bone, which may be determined by, for example, a bone density determination, a knowledge of the patient's medical data, and/or data on the particular bone into which the plug is being inserted.

The above embodiments of the expansion member are intended for use when the plug is inserted into a bone tunnel second end first. However, in another system 11 and method of use the plug 20' is inserted first end 202' First (see FIGS. 10A and 10B). In order to deploy the arms 205', the expansion member must be pulled into the bore 206' from a distal end of the bone tunnel 42. This is accomplished by means of an expansion unit that comprises an elongated manipulator 33 that has an axial dimension sufficiently small to pass through the plug member's bore 206'. The expansion unit also comprises an expansion member 34 that is engagable with, such as being frangibly affixed at, a second end 344 to a first end 332 of the manipulator 33.

The expansion member 34 has an insertion portion 341 adjacent the second end 344 that is adapted to separate the arms 205' upon the manipulator's being pulled in a proximal direction to progressively move the expansion member's insertion portion 341 into the bore 206' (FIG. 10B). The manipulator 33 is detachable from the expansion member 34 upon the expansion member's being inserted as far as possible given the dimensions of the bone tunnel 42 into the plug member's bore 206'.

Another embodiment of an expansion member 36 (FIG. 8) permits the insertion of a bone plug to a desired predetermined force level. This expansion member 36 is based upon the concept of a shear pin, and includes a generally conical body 360 tapering from a first end 362 to a second end 364. A radial hole 366 is dimensioned to house a pin 361, which is adapted to break at a predetermined force level. Surrounding the body's first end 362 and affixed to the pin 361 is a collar 365, which has means for being driven by, for example, a hex driver; alternatively, the collar 365 may be affixed to a driving device. The collar 365 is dimensioned to freely rotate about the body's first end 362.

In use, then, when the driver is turned in order to insert the expansion member 36 into the plug, rotation is permitted until the predetermined force level is reached, at which point the pin 361 breaks, and the collar 365 will continue to rotate independently of the body 360. The driver and collar 365 can then be removed.

A fourth embodiment of the bone plug includes a duplex plug member 22 that is essentially a composite of two of the above-described plugs, second end to second end (FIG. 9A). The duplex plug member 22 has two outer ends 222, 224 and a first axial bore 226 that extends from a first outer end 222 and a second axial bore 227 that extends from a second outer end 224. Preferably a narrower third axial bore 228 is positioned in connecting relation to the first and second axial bores 226, 227 to form a unitary axial bore that extends between the outer ends 222, 224.

The duplex plug member 22 further has a first 225 and a second 223 set of interleaving arms disposed about the first and the second bores 226, 227. The arms are affixed at a central portion 221 between the outer ends 222, 224, and each set of arms is separable at their outer ends between an insertion position wherein the arms are relatively close packed and a position wherein the arms are flared, each arm remaining in overlapping relation to an adjacent arm in a set.

This bone plug system also includes at least one expansion member that has an insertion portion adapted to separate one set of arms upon progressive entry into one of the bores. In a preferred embodiment a combination of the two systems discussed above is used with one each of the expansion members 32, 34, with the expansion member 34 being inserted from the distal end 224 (as in FIGS. 10A and 10B) and the expansion member 32 then inserted from the proximal end 222 (as in FIGS. 11A and 11B).

Alternatively, the duplex plug 22 may also be expanded by means of coupled expansion members (FIG. 9B). In this embodiment a bottom expansion section 34 tapers toward a bottom end and has a bore 340 therethrough. Bottom expansion section 34 is insertable into the plug's distal bore 227 and is dimensioned to expand arms 223 upon progressive insertion thereinto.

A rod 341 is provided that has a length at least sufficient to span the bores 226, 227, 228. The rod 341 also has a bottom portion dimensioned for freely sliding within the bore 340 that is inserted therethrough, and a bottom protrusion 342 dimensioned to prevent entry into the bore 340. The rod 341 further has a top threaded portion 343 extending above the bottom expansion section 34.

A top expansion section 35 tapers toward a top end and has a bore 350 that is at least partially threaded, the threads dimensioned for engagement with the rod's top threaded portion 343. Thus, when the top expansion section 35 is rotated in a direction to move it down the rod 341, it is brought closer to the bottom expansion section 34. These coupled motions will serve to expand both sets of arms 223, 225, expanding the plug sections 34, 35 for plugging a bone canal.

A further aspect of the present invention includes a differentially expandable bone plug 23 (FIG. 12), which has an outer periphery 230 disposed about a longitudinal axis 236 and a plurality of, here three, radially arrayed sectors 238. Each sector 238 has a plurality of interleaving arms 235 disposed about the outer periphery 230. The arms 235 are affixed at their second ends as above, and are flarable at a first end 233 between an insertion position wherein the arms are relatively close packed and a position wherein the arms 235 are flared, each arm 235 remaining in overlapping relation to an adjacent arm 235'. A portion of a first end 233 of each arm 235 is adjacent an insertion axis 239 when in the insertion position.

This system includes a plurality of expansion members 31 as above (FIG. 6), each having an insertion portion 311 adapted to flare the arms 235 of a sector 238 upon insertion along the insertion axis 239 from the plug member's first end 232 and progressive movement toward the plug member's second end.

Figure 13:
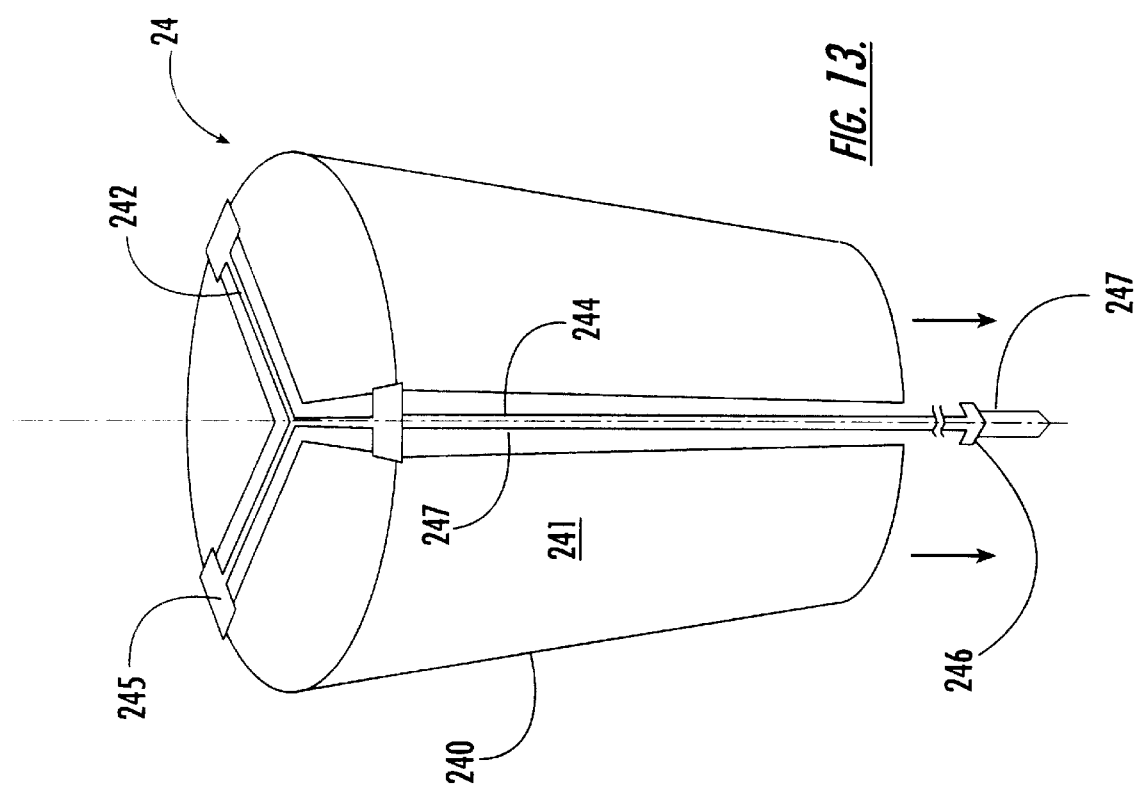
FIG. 13 is a side perspective view of a tripartite differentially deployable bone plug.
Figure 12:
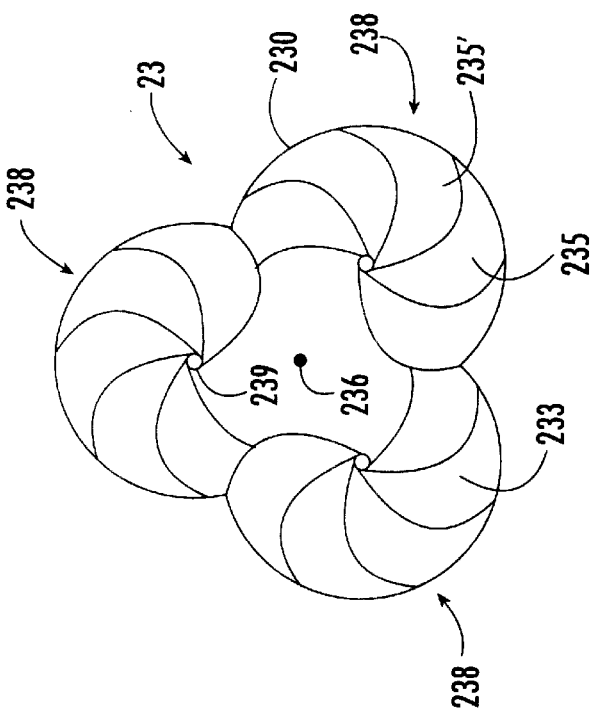
FIG. 12 is a top plan view of a tripartite differentially expandable bone plug.

Yet another aspect of the present invention includes a differentially deployable bone plug 24 (FIG. 13). This bone plug 24 has an outer periphery 240 surrounding an insertion axis 246. A plurality of radially arrayed sectors 241 is provided, each sector 241 differentially movable in an axial direction between an insertion position and a downwardly deployed position. The sectors 241 are supported by a sector frame 242, which has means for supporting each sector, means for preventing an upward movement of each sector above the insertion position, and means for permitting each sector to be moved downward from the insertion position to the deployed position. An exemplary frame 242 comprises deformable side rails 244 and a central rail 247 upon which each sector 241 is downwardly movable and top rails 245 joining the side rails 244 and central rail 247 that prevent each sector 241 from moving upward above the insertion position. Pressure upon any sector 241 deploys that sector 241 downward into the bone cavity 42 until a stop 246 in the side rail 244 is met. Such a differentially deployable plug 24 permits a bone cavity having a nonuniform shape to be plugged with a single device.

A method is also provided as an aspect of the present invention for preventing flowing material from extruding beyond a predetermined location in a tunnel or canal 42 of a bone 40. The method comprises the steps of providing a bone plug such as described above, for example, the bone plug 20, 20', or 20".

In a first embodiment of the method of use, shown in FIGS. 10A and 10B, the expansion unit is inserted into a bone canal 42, with the expansion member 34 inserted first. The bone plug 20' is next inserted into a bone canal 42 to a desired location, the first end 202' first. Then the manipulator 33 is pulled in a direction out of the bone canal 42, until the expansion member 34 is seated within the plug's bore 205'.

Figure 11B:
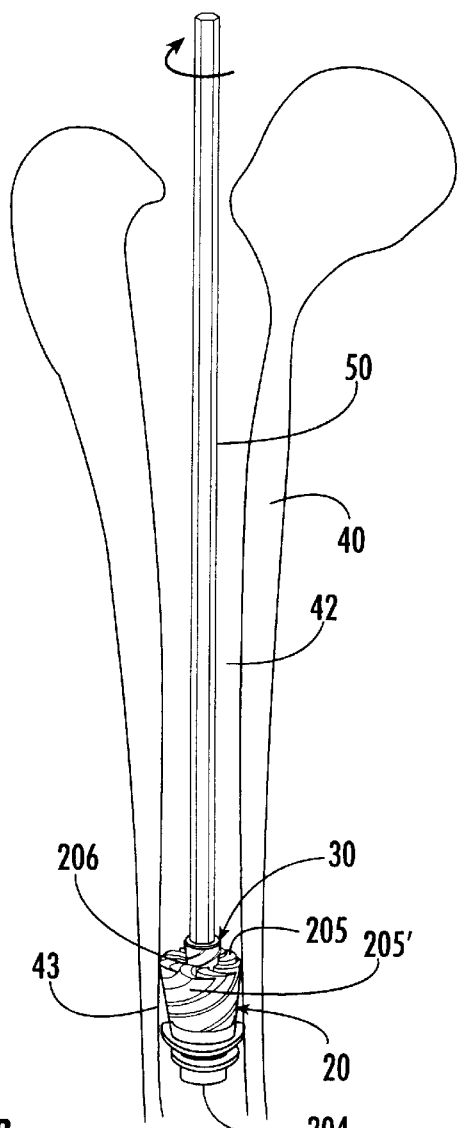
FIG. 11B illustrates the bone plug arms being expanded radially outward with an insertion of an expansion member.

In a second embodiment of the method of use, shown in FIGS. 11A and 11B, the bone plug 20 is inserted into a bone canal 42 to a desired location, the second end 204 first.

Next the arms 205 are expanded to a position wherein the arms 205 are flared, such that each arm tail section 203 remains in overlapping relation to an adjacent arm 205'. In a preferred embodiment, this expanding step comprises progressively inserting a tapered member such as screw 30 into the bore 206, the smaller second 304 end inserted first. A hexagonal driver 50 can be used, for example, to advance the screw 30 into the plug member bore 206. The expanding step is continued until the plug 20 is securely pressed against a wall 43 of the bone tunnel 42.

With the bone plug 20' or 20 in place, the next step in the procedure can be undertaken, such as the insertion of an implant, with the tunnel 42 blocked against the passage of flowing material.

It may be appreciated by one skilled in the art that additional embodiments may be contemplated, including differently shaped plugs for different bone canals and differently shaped arms that also continue to overlap upon progressive expansion.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are see forth in the appended claims.

What is claimed is:

1. A bone plug having a plurality of interleaving arms disposed about an insertion axis extending from a first end, the arms affixed at a second end and flarable at the first end between an insertion position wherein the arms are relatively close packed and an expanded position wherein the arms are flared, each arm having a generally paisley shape in axial cross section, a paisley head section facing generally toward the insertion axis and a paisley tail section facing generally outward, each arm remaining in overlapping relation to an adjacent arm, the plug first end adapted to receive an expansion member along the insertion axis for flaring the arms upon a progressive insertion thereof, the plug further having a deformable circumferential flange adjacent the second end.

2. A bone plug system comprising:
a plug member having a plurality of interleaving arms disposed about an insertion axis, the arms affixed at a second end and separable at a first end axially opposed to the second end between an insertion position wherein the arms are relatively close packed and an expanded position wherein the arms are radially flared, each arm remaining in overlapping relation to an adjacent arm, each arm having an inner edge, the inner edges of the arms defining the insertion axis when in the insertion position; and
an expansion member operable with the plug member having an insertion portion adapted to flare the arms upon progressive entry from the plug member first end along the insertion axis, wherein the expansion member tapers outward from a second end to a first end and comprises a screw having helical outer threads extending from the second end and the plug member has a helical groove along an inner wall defining a bore encompassing the insertion axis, the groove adapted for mating with the screw threads.

3. A bone plug system comprising:
a plug member having a plurality of interleaving arms disposed about an insertion axis, the arms affixed at a second end and separable at a first end axially opposed to the second end between an insertion position wherein the arms are relatively close packed and an expanded position wherein the arms are radially flared, each arm remaining in overlapping relation to an adjacent arm, each arm having an inner edge, the inner edges of the arms defining the insertion axis when in the insertion position; and
an expansion member operable with the plug member having an insertion portion adapted to flare the arms upon progressive entry from the plug member first end along the insertion axis, wherein the expansion member tapers outward from a second end to a first end and has means for being driven at the first end comprising means for engaging a driver frangibly affixed to the expansion member first end, the frangibility having a predetermined force value, thereby permitting a driving of the expansion member until the predetermined force value is reached.

4. A bone plug system comprising:
a plug member having a plurality of interleaving arms disposed about an insertion axis, the arms affixed at a second end and separable at a first end axially opposed to the second end between an insertion position wherein the arms are relatively close packed and an expanded position wherein the arms are radially flared, each arm remaining in overlapping relation to an adjacent arm, each arm having an inner edge, the inner edges of the arms defining the insertion axis when in the insertion position; and
an expansion member operable with the plug member having an insertion portion adapted to flare the arms upon progressive entry from the plug member first end along the insertion axis, wherein the expansion member tapers outward from a second end to a first end and has means for being driven at the first end comprising a hexagonal indentation for mating with a hexagonal driver.

5. A bone plug system comprising:

a plug member having a plurality of interleaving arms disposed about an insertion axis, the arms affixed at a second end and separable at a first end axially opposed to the second end between an insertion position wherein the arms are relatively close packed and an expanded position wherein the arms are radially flared, each arm remaining in overlapping relation to an adjacent arm, each arm having an inner edge, the inner edges of the arms defining the insertion axis when in the insertion position, the plug member further having a deformable circumferential flange adjacent the second end; and an expansion member operable with the plug member having an insertion portion adapted to flare the arms upon progressive entry from the plug member first end along the insertion axis.

6. The bone plug system recited in claim 1, wherein each arm has a generally paisley shape in axial cross section, a paisley head section facing generally toward the insertion axis and a paisley tail section facing generally radically outward.

7. The bone plug system recited in claim 6, wherein each paisley head section is contoured to form a generally circular bore encompassing the insertion axis in axial cross section.

8. The bone plug system recited in claim 6, wherein the tail sections are sufficiently long that in the expanded position each tail section remains in overlapping relation to an adjacent arm.

9. The bone plug system recited in claim 6, wherein a tail edge of each tail section extends generally axially.

10. The bone plug system recited in claim 6, wherein a tail edge of each tail section extends in generally helically about the axial direction.

11. The bone plug system recited in claim 1, wherein the flange comprises a first flange and the plug member further has a second circumferential flange in spaced relation to the first flange between the first flange and the first end, the second flange having a circumference greater than a circumference of the first flange.

12. The bone plug system recited in claim 1, wherein the plug member has a generally elliptical axial outer cross-sectional shape.

13. The bone plug system recited in claim 1, wherein the expansion member tapers outward from a second end to a first end.

14. The bone plug system recited in claim 13, wherein the expansion member has means for being driven at the first end.

15. The bond plug system recited in claim 14, wherein the means for being driven comprises means for engaging a torque wrench, for permitting a driving of the expansion member until a predetermined torque a is reached.

16. The bone plug system recited in claim 13, wherein the expansion member comprises a truncated conical element adapted for press fitting within the plug member along the insertion axis.

17. The bone plug system recited in claim 16, wherein the conical element has means for resisting a movement out of the plug member.

18. The bone plug system recited in claim 17, wherein the movement-resisting means comprises a plurality of barbs protruding from an outer surface, the barbs each canted generally toward the conical element second end.

* * * * *